(12) United States Patent
Dunne

(10) Patent No.: US 10,285,829 B2
(45) Date of Patent: May 14, 2019

(54) SYSTEM AND METHOD FOR FABRICATING CUSTOM MEDICAL IMPLANT DEVICES

(71) Applicant: 3D Systems, Inc., Rock Hill, SC (US)

(72) Inventor: Patrick C Dunne, Lafayette, CA (US)

(73) Assignee: 3D SYSTEMS, INC., Rock Hill, SC (US)

( * ) Notice: Subject to any disclaimer, the term of this patent is extended or adjusted under 35 U.S.C. 154(b) by 911 days.

(21) Appl. No.: 14/709,773

(22) Filed: May 12, 2015

(65) Prior Publication Data
US 2015/0320956 A1 Nov. 12, 2015

Related U.S. Application Data

(60) Provisional application No. 61/991,714, filed on May 12, 2014.

(51) Int. Cl.
*B33Y 10/00* (2015.01)
*B29C 33/52* (2006.01)
(Continued)

(52) U.S. Cl.
CPC ............ *A61F 2/82* (2013.01); *A61F 2/30942* (2013.01); *A61F 2/92* (2013.01); *A61M 16/0434* (2013.01);
(Continued)

(58) Field of Classification Search
CPC .................. A61F 2/04; A61F 2002/046; A61F 2240/002; A61F 2/30942;
(Continued)

(56) References Cited

U.S. PATENT DOCUMENTS 5,556,426 A 9/1996 Popadiuk et al.
6,175,422 B1 1/2001 Penn et al.
(Continued)

FOREIGN PATENT DOCUMENTS

JP 2002239013 8/2002
JP 2007535418 12/2007
(Continued)

OTHER PUBLICATIONS

PCT International Search Report for the International Searching Authority for PCT/US2015/030293, dated Aug. 5, 2015 (4 pages).
(Continued)

*Primary Examiner* — Suba Ganesan
(74) *Attorney, Agent, or Firm* — Staniford Tomita LLP

(57) ABSTRACT

A method for creating tubular inserts is useful for creating custom fitted inserts that correspond to the anatomy of a patient and solve the problem of pressure points, wear of the implant, damage to surrounding tissue, and denting. Surface measurements of the affected portion of a patient's internal cavity are obtained. Those measurements are used to design a core. The core is 3D printed with a soluble material. The core is wrapped with a thin filament or film such that the contours from the core develop on the outer surface of the covering. The covering is hardened and the core is dissolved away, leaving a custom-made implant device that can be deposited in the patient's cavity.

15 Claims, 8 Drawing Sheets

(51) Int. Cl.

| | | |
|---|---|---|
| *B29C 70/30* | (2006.01) | |
| *A61F 2/82* | (2013.01) | |
| *A61M 16/04* | (2006.01) | |
| *B29C 53/60* | (2006.01) | |
| *B29C 53/82* | (2006.01) | |
| *A61F 2/92* | (2013.01) | |
| *A61F 2/30* | (2006.01) | |
| *B33Y 80/00* | (2015.01) | |
| *G01R 33/56* | (2006.01) | |
| *B29C 53/58* | (2006.01) | |
| *B29C 64/106* | (2017.01) | |
| *B29K 67/00* | (2006.01) | |
| *B29L 31/00* | (2006.01) | |
| *A61F 2/88* | (2006.01) | |
| *A61F 2/04* | (2013.01) | |
| *B29C 41/14* | (2006.01) | |
| *A61B 5/055* | (2006.01) | |
| *A61B 5/107* | (2006.01) | |
| *A61B 6/03* | (2006.01) | |
| *A61B 6/00* | (2006.01) | |
| *B29C 53/66* | (2006.01) | |
| *B29C 64/00* | (2017.01) | |

(52) U.S. Cl.
CPC ............ *B29C 33/52* (2013.01); *B29C 53/587* (2013.01); *B29C 53/60* (2013.01); *B29C 53/822* (2013.01); *B29C 64/106* (2017.08); *B29C 70/30* (2013.01); *B33Y 80/00* (2014.12); *G01R 33/5608* (2013.01); *A61B 5/055* (2013.01); *A61B 5/1075* (2013.01); *A61B 5/1076* (2013.01); *A61B 5/1077* (2013.01); *A61B 6/032* (2013.01); *A61B 6/50* (2013.01); *A61B 6/504* (2013.01); *A61F 2/88* (2013.01); *A61F 2/885* (2013.01); *A61F 2002/046* (2013.01); *A61F 2002/30948* (2013.01); *A61F 2002/30957* (2013.01); *A61F 2002/30958* (2013.01); *A61F 2210/0071* (2013.01); *A61F 2210/0076* (2013.01); *A61F 2240/002* (2013.01); *A61M 16/0406* (2014.02); *A61M 2205/02* (2013.01); *A61M 2207/00* (2013.01); *B29C 41/14* (2013.01); *B29C 53/66* (2013.01); *B29C 64/00* (2017.08); *B29K 2067/046* (2013.01); *B29K 2911/00* (2013.01); *B29L 2031/753* (2013.01); *B29L 2031/7532* (2013.01); *B29L 2031/7546* (2013.01); *B33Y 10/00* (2014.12)

(58) Field of Classification Search
CPC ............ B29C 2033/3871; B29C 33/38; B29C 33/3835; B29C 64/112; B29C 64/165; B29C 70/30; B33Y 10/00; B19C 33/52
See application file for complete search history.

(56) References Cited

U.S. PATENT DOCUMENTS

| | | | |
|---|---|---|---|
| 7,815,826 B2 | 10/2010 | Serdy et al. | |
| 8,025,637 B2 | 9/2011 | Weber et al. | |
| 9,163,333 B2 | 10/2015 | Vad et al. | |
| 9,468,494 B2 | 10/2016 | O'Sullivan et al. | |
| 2003/0211130 A1* | 11/2003 | Sanders | A61L 27/18 424/423 |
| 2004/0116997 A1* | 6/2004 | Taylor | A61F 2/07 623/1.11 |
| 2005/0043783 A1* | 2/2005 | Amis | A61F 2/88 623/1.22 |
| 2005/0186361 A1 | 8/2005 | Fukuda et al. | |
| 2007/0293936 A1* | 12/2007 | Dobak, III | A61F 2/07 623/1.13 |
| 2011/0060445 A1 | 3/2011 | Heenan | |
| 2012/0013043 A1 | 1/2012 | Weber et al. | |
| 2013/0150963 A1 | 6/2013 | Johnson | |
| 2013/0197657 A1* | 8/2013 | Anca | A61F 2/07 623/23.7 |
| 2013/0296998 A1 | 11/2013 | Leotta et al. | |
| 2016/0000976 A1 | 1/2016 | Vad et al. | |
| 2016/0106536 A1* | 4/2016 | Chui | A61F 2/20 623/9 |
| 2017/0027641 A1 | 2/2017 | O'Sullivan et al. | |

FOREIGN PATENT DOCUMENTS

| | | |
|---|---|---|
| JP | 2013022456 | 2/2013 |
| WO | 03/096308 | 11/2003 |

OTHER PUBLICATIONS

PCT Written Opinion of the International Searching Authority for PCT/US2015/030293, dated Aug. 5, 2015 (5 pages).
PCT International Search Report for the International Preliminary Report on Patentability for PCT/US2015/030293, dated Nov. 24, 2016 (7 pages).
Third Office Action for Japanese Patent Application No. 2016-567836, dated Aug. 30, 2018 (5 pages).
Second Office Action for Japanese Patent Application No. 2016-567836, dated May 17, 2018 (3 pages).
First Office Action for Japanese Patent Application No. 2016-567836, dated Oct. 19, 2017 (3 pages).

* cited by examiner

SYSTEM AND METHOD FOR FABRICATING CUSTOM MEDICAL IMPLANT DEVICES

CROSS REFERENCE TO RELATED APPLICATIONS

This application claims priority to U.S. Provisional Patent Application No. 61/991,714, "System And Method For Fabricating Custom Medical Implant Devices" filed May 12, 2014 which is hereby incorporated by reference in its entirety.

BACKGROUND

The flow of air and blood within the body are vital, life-sustaining functions and in some situations, implanted medical devices can be used to maintain the proper flow of air and/or blood within a patient after an injury. For example, the flow of air may be compromised by injuries to the trachea and bronchi (tracheobronchial injuries, or "TBIs"). Such injuries can place a patient in immediate critical condition from obstruction of the airway and in imminent critical condition from oxygen insufficiency in the body. TBIs are a common medical condition, occurring most frequently from blunt or penetrating trauma to the neck or chest, inhalation of harmful fumes or smoke, or aspiration of liquids or objects.

Similarly, the flow of blood may be compromised by injured and/or blocked blood vessels. A stent is a known vascular implant used to help keep the vessel open. However, vascular plaque is typically non-uniform and often forms in bulky occlusions. These occlusions place stress on conventional stents via point forces that increase the risk of hinging or denting of the stent. Denting is caused by an inherent weakness of conventional stents where a vaso-occlusion drives a portion of the stent into the luminary space, thereby substantially enhancing the blockage effect of the vaso-occlusion. Denting can lead to increased collection of thrombus or flow distortions, which are problematic and can increase stenosis.

What is needed is a system and method for creating custom fitted inserts that correspond to the anatomy of the patient and solve the problem of pressure points, wear of the implant, damage to surrounding tissue, denting, and other problems associated with placing foreign components in a patient's body.

SUMMARY OF THE INVENTION

In various embodiments, a method for creating a tubular insert. The method may use internal surface measurements from the affected portion of a patient's internal cavity. In an embodiment, surface measurements can be obtained from a magnetic resonance imaging (MRI) scanner, a computed tomography (CT) scanner, X-ray computed tomography (X-ray CT), a computer aided design (CAD) file or any other suitable anatomical measurement data. Those measurements may be used to design a core. For example, the inner surface measurements of a patient's trachea can be used to create core design data for a core having an outer surface that corresponds to the inner surface of the trachea. The contours on the inner surfaces of the trachea can be designed into the contours of the outer surface of the core design data which can be stored in a digital format on a memory device.

The core data can be used to create a core. In an embodiment, the core can be fabricated with a 3D printer by sequentially fusing multiple planar layers where each layer can be a cross section of the core. The 3D printer can emit a core material in a liquid form from a print head that can harden in a pattern that matches the cross section of the core. In an embodiment, the core material can be a thermo-plastic material that is heated to a temperature that is higher than the melting temperature of the core material. The core material can be emitted by the print head and it can cool into a solid material. The core can be fabricated by depositing one planar layer of the core. The next subsequent planar layer of the core can be deposited over and fused to the prior planar layer. This process can continue until the core is complete. In an embodiment, the core can be 3D printed with a soluble material as a hollow and/or high porosity structure. The outer surface of the core may have a higher density or be a solid material while the inner portion of the core can be porous or have open areas.

The core can be wrapped with a thin filament or film that can harden around the core. In an embodiment, the filament or film material can be heated while it is wrapped around the core. The filament or film material then cools and harden around the core. The contours from the outer surface of the core can formed on the outer surface of the covering. The covering can be hardened and the core can be exposed to a solvent and dissolved away, leaving a custom-made implant device that can be deposited in the patient's cavity. In an embodiment, the hollow and/or porous structure of the core can allow the solvent to more easily dissolve the core.

DETAILED DESCRIPTION

The present invention is directed towards a method for creating a custom fitting tubular insert for insertion into the inner cavities of a patient. The inner cavities of a patient may include, but are not limited to, the trachea, bronchi, vessels, any part of the airway system, circulatory system, urinary system, and/or digestive system. The method can create a custom-made insert to fit the unique contours of an individual along any portion of a patient's inner cavities. A custom implant that corresponds to the anatomy of the patient can be very desirable because an implant that does not match the patient's anatomy can be uncomfortable and cause injury. For example, cylindrical implants used to keep airway passages open are problematic because they create pressure points that wear down the patient's trachea. Thus, a custom fitting structure would greatly improve the successful use of medical implants within patients.

In an embodiment, the method for creating a custom tubular insert that corresponds to the patient's anatomy can comprise obtaining surface measurements of the internal surface of the damaged portion of the patient, using the surface measurements to create a mold design, using the core design to 3D print a core by sequentially fusing a plurality of planar layers wherein the outer surface of the core matches or closely corresponds to the patient's internal anatomy measurements. In an embodiment, the core is made of soluble material. An insert material can be wrapped around the mold. In an embodiment, the insert material can be a thermoplastic that can be heated to be a flexible material that can conform to the outer surface of the core. The insert material cool and harden on the core to create an insert. In order to remove the core from the insert, the core can be dissolved by exposing the core to a solvent. For example, if the core material is water soluble such as sugar, the core can be exposed to water to dissolve the core. The custom insert will match or closely corresponds to the patient's internal anatomy and will fit within the non-uniform surfaces of the individual patient's body.

Figure 1:
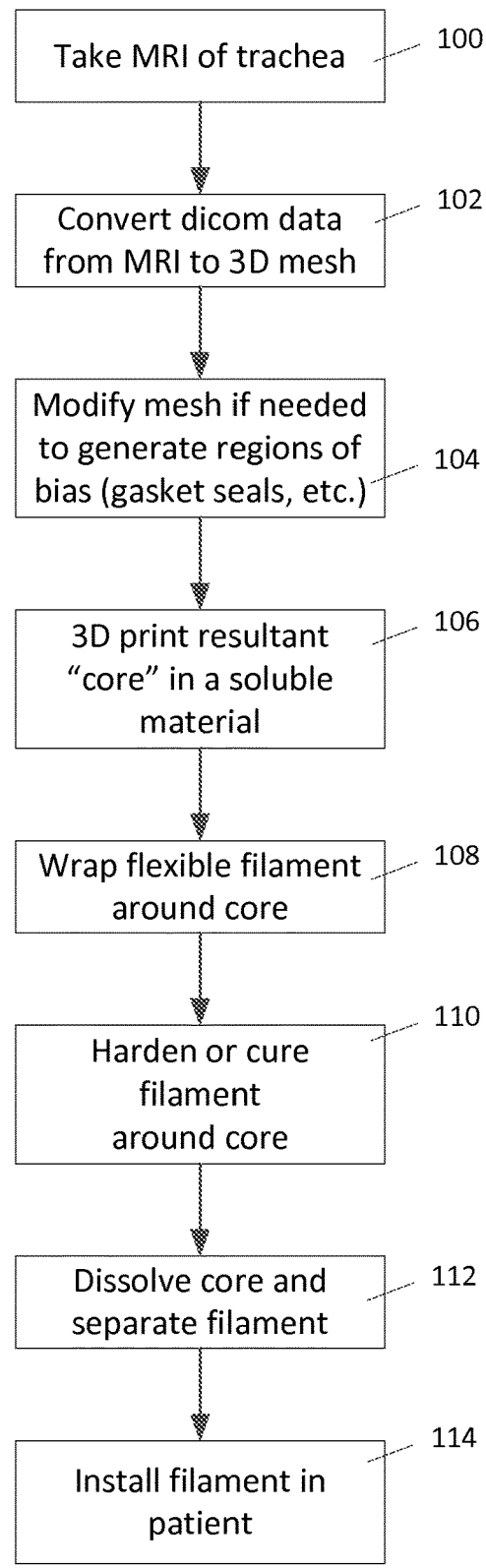
FIG. 1 illustrates an embodiment of a flow chart showing a method for creating a custom fitting implant.

FIG. 1 illustrates an embodiment of a method for making a custom insert. In the first step, MRI scanning is used to obtain surface measurements of a trachea 100 including the internal diameter surfaces of the trachea. In other embodiments, the surface measurements can be obtained from computed tomography (CT) scanner, X-ray computed tomography (X-ray CT), a computer aided design (CAD) file or any other suitable anatomical measurement data. In an embodiment, the surface measurements can be in a Digital Imaging and Communications in Medicine (DICOM) standard that can be used for handling, storing, printing, and transmitting information in medical imaging. DICOM includes a file format definition and a network communications protocol. The communication protocol is an application protocol that uses TCP/IP to communicate between systems. DICOM files can be exchanged between two entities that are capable of receiving image and patient data in DICOM format. DICOM can enable the integration of scanners, servers, workstations, printers, and network hardware from multiple manufacturers into a picture archiving and communication system (PACS).

The DICOM data from the MRI (or other source) is converted to 3D mesh 102. For example the negative internal space can be extracted from the DICOM data to create the 3D mesh 102. The mesh 102 can be modified as needed to generate regions of bias, such as gasket seals 104 which can be compressed against the inner surfaces of the trachea. The interior surface contours of the trachea can correspond to the outer surface of the care design. A core is 3D printed in a soluble material 106. For example, the core can be printed in solid sugar which is water soluble. During the 3D printing process, a series of planar layers of soluble material 106 can be sequentially deposited by a 3D printer and fused together to form the core structure.

A flexible filament can be wrapped around the core 108. The filament is hardened, or cured, around the core 110. In an embodiment the flexible filament can be a thermoplastic material. Prior to wrapping the filament around the core, the filament can be heated to increase the pliability of the material. The filament can then be cooled to harden the filament so that the filament conforms to the outer surface of the core. In other embodiments, the filament can be wrapped around the core in a flexible uncured state. The filament can be exposed to a curing agent which can be a catalyst or exposure to light, heat or other curing methods. The curing can harden the filament around the core. In an embodiment the 3D mesh 102 can be adjusted to compensate for the thickness of the filament that is placed around the 3D mesh 102 so the outer surfaces of the filament match the inner surfaces of the trachea based upon the MRI (or other measurement) data.

The core is dissolved, leaving the separated filament 112. For example, the filament insert and core can be placed in a solvent to dissolve the core so that the filament insert can be separated from the core. In an embodiment, the core can be made of a water soluble material and the filament can be non-water soluble. The filament insert and core can be placed in water, the core can dissolve in the water and the filament can be separated from the core. In an embodiment, the core can be fabricated as a porous and/or hollow structure. The porosity and/or hollow construction of the core 108 can allow the water to more easily dissolve the core sugar material. In other embodiments, any other process can be used to separate the core from the filament insert or other tubular insert. For example, the core can be made of a material, such as a wax-based material, that can be heated and melted to separate the core from the filament insert. Another example is a core that incorporates physical features, such as internal features, that enable the core to mechanically change shape to allow the tubular insert to be separate from the core without heat or a solution. The resulting filament insert structure can be installed in a patient 114.

Figure 2:
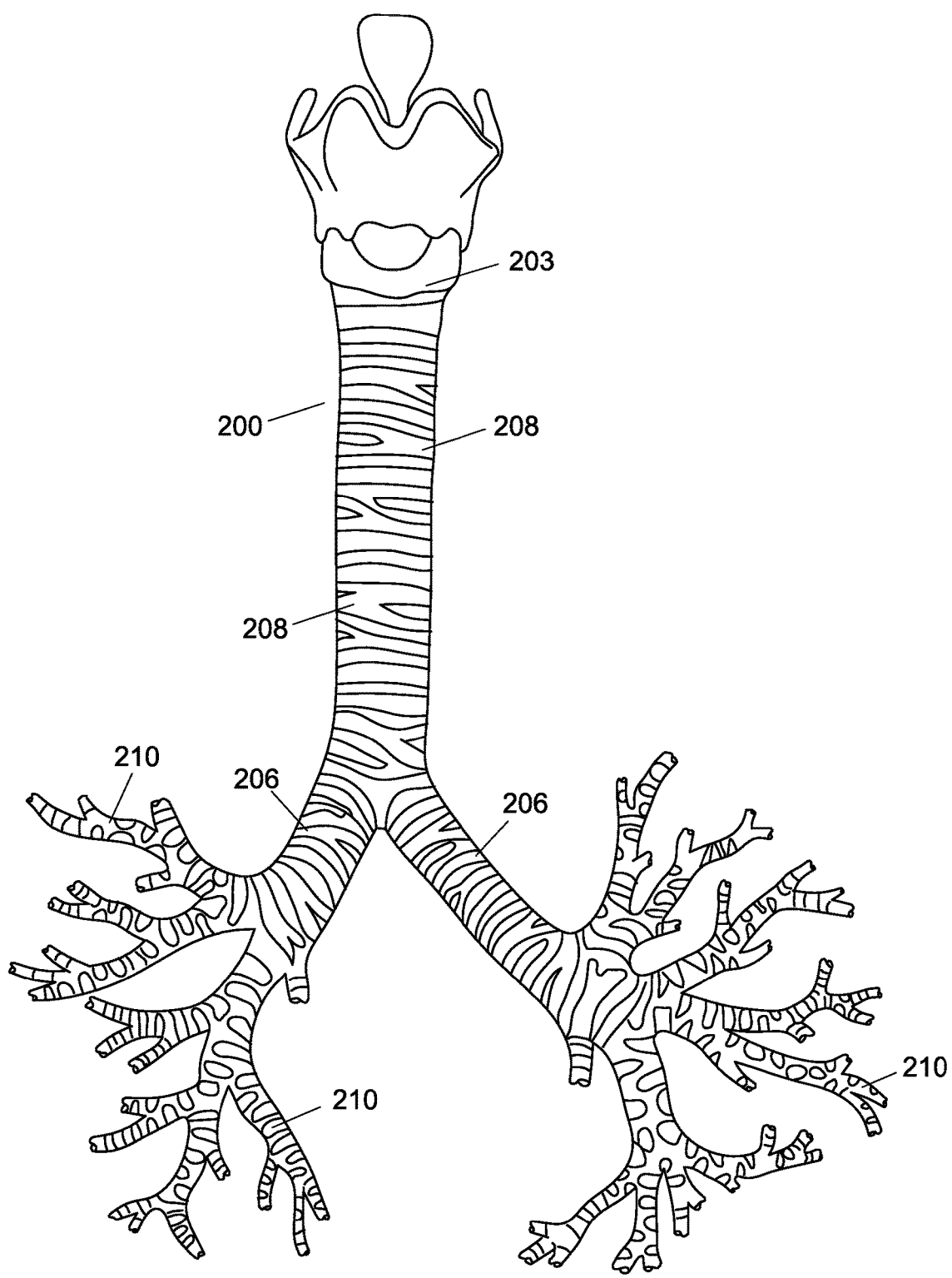
FIG. 2 illustrates a human respiratory system.

In an embodiment, the inner surfaces being measured can be that of the trachea. As illustrated in FIG. 2, the trachea 200 is situated between the lower end of the larynx 203 and the center of the chest where it splits into the two bronchi 206. The trachea 200 can be stabilized and may be kept open by rings 208 made of cartilage that surround the trachea 200. The bronchi 206 split into smaller branches 210 and then to bronchioles that supply air to the alveoli, the tiny air-filled sacs in the lungs responsible for absorbing oxygen.

The inner surfaces of the trachea 200 cavity are non-uniform because the trachea is lined by taenidial folds and mucosal folds. These folds create unique contours within the inner surface of a patient's trachea. An insert that does not fit well within the patient's trachea can impair mucociliary clearance, be difficult to insert, migrate, cause airway obstruction, cause inflammation and formation of granulation tissue that infiltrates the insertion and results in obstruction. A poor fitting insert that causes such complications may require removal, which risks other complications, such as bodily injury that can result in profuse bleeding. In other embodiments, the inner surfaces of the patient's cavity can have a branch configuration. The branch configuration may include a trachea 200 and bronchial tubes 206. In still other embodiments, the insert can be used for any other patient anatomy such as branched artery sections of a patient.

Surface measurements of the internal surface of the damaged portions of the patient may be obtained via scanning and/or imaging methods which yield data on the contours of the affected structures of the patient. In an embodiment, the internal surface measurements of the trachea 200 can be obtained using MRI scanning data. MRI surface data is desirable because it includes data on the contoured surface of an inner cavity, which will be specific and unique to the patient. In other embodiments, the contoured surface of an inner cavity can be obtained through: real-time MRI, dynamic MRI, cine MRI (CMRI) techniques, CT scanning, fiber optic visualization, X-ray computed tomographs, computer aided design (CAD) file and/or any other suitable processes. Such images and internal surface data may be correlated with endoscopy when necessary.

Figure 3:
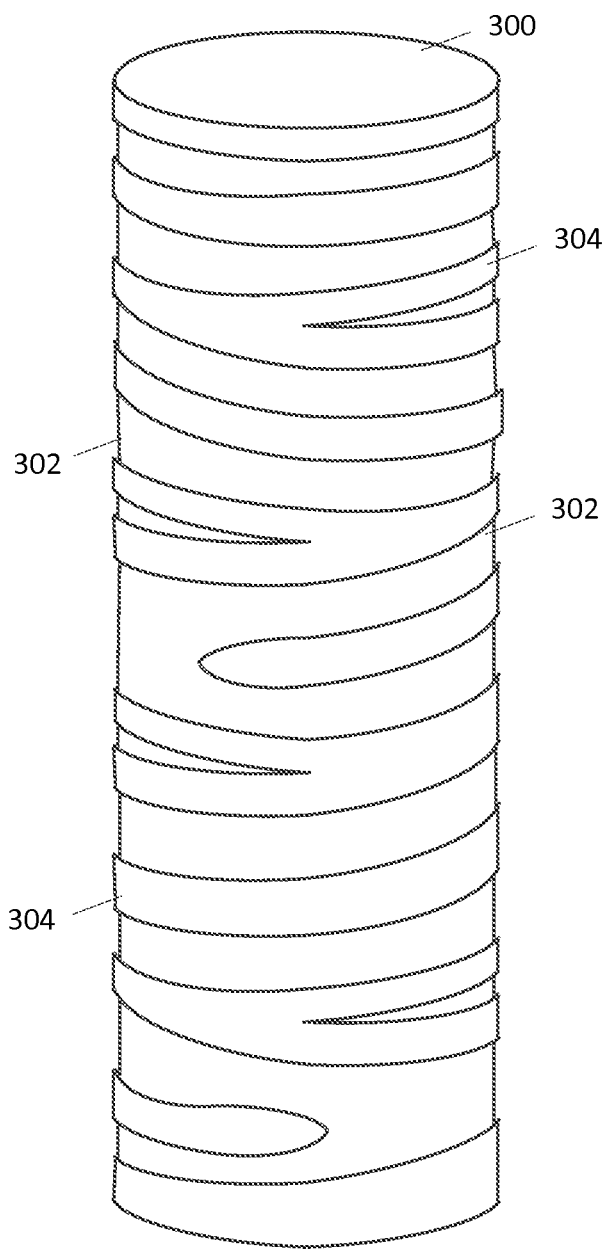
FIG. 3 illustrates an embodiment of a patient specific custom core.

The internal surface measurement data can be used to create a core design that has an external surface that matches or corresponds to the internal surface of the trachea 200. A 3D printer can use the core design to fabricate a core. In an embodiment, the core can be fabricated by depositing and sequentially fusing a plurality of planar cross section layers of the core. FIG. 3 illustrates an example of a core 300 having external surfaces that match or correspond to the internal or inner diameter surfaces of the patient's trachea. The inner surfaces of the patient's trachea will have unique concave 302 and convex 304 aspects. This custom core surface can match the inner surface of any cavity. This custom designed core and insert are important to fit and comfort when the insert implant is placed within the trachea. Good fit is important in order to avoid further endangering the patient via denting of the insert and damaging of surrounding tissue, and to avoid premature wear of the insert, and to avoid migration of a poorly fitted insert. The insert implant may only be as long as needed to support a weak or injured portion of the patient's trachea. By creating a custom insert implant that matches the patient's trachea, pressure of the inner surfaces of the trachea against the outer surfaces of the insert can be evenly distributed which can prevent high pressure contact areas that can result in injury.

For example, for a tracheal stenosis patient, a physician may order an MRI, and CMRI to obtain axial, coronal, and sagittal images or any other measurements as described above. These images would allow the physician to detect the location and movement of the trachea to identify where an insert is needed and use the images to make a uniquely contoured insert, as discussed earlier. For example, a patient with tracheal compression may have unique dynamic components contributing to airway obstruction, such as tracheomalacia, mass lesions, or anomalous vasculature. Such unique contours are captured by the MRI imaging, giving information on how to contour the necessary insert. Moreover, imaging may show the degree of airway compromise, which allows for the design of a modified insert having custom areas of reinforcement as needed.

The MRI (or other measurement methods) of the inner surface of the patient's cavity produces DICOM data which is converted to 3D mesh data STereoLithography (STL) which is a file format native to the stereolithography CAD software created by 3D Systems. STL files describe the surface geometry of a three-dimensional object. An STL file describes a raw unstructured triangulated surface by the unit normal and vertices (ordered by the right-hand rule) of the triangles using a three-dimensional Cartesian coordinate system. Stereolithography machines are 3D printers that can build any volume shape as a series of slices. Ultimately these machines require a series of closed 2D contours that are filled in with solidified material as the parallel planar layers are fused together. A natural file format for such a machine would be a series of closed polygons corresponding to different Z-values. However, since it's possible to vary the layer thicknesses for a faster though less precise build, it was easier to define the model to be built as a closed polyhedron that can be sliced into many parallel planar cross sections at the necessary horizontal levels.

The surface measurements in the 3D mesh data can be used to create a core design having all the concave and convex surfaces of the patient's inner cavity precisely as they are in the patient. The core design being a mold of the contours of the inner cavity, substantially like a dentist may use bite marks and tooth imprints to mold a dental insert. As illustrated in FIG. 3, the core 300 is a mold of the inner surface of the patient's cavity, having the three dimensional contours that match or closely correspond to the patient's trachea anatomy. Implant devices having a surface geometry that matches or closely corresponds to the patient's trachea anatomy can be crafted from the core 300. In an embodiment, the 3D mesh data obtained is then modified as needed to generate regions of bias.

In an embodiment, the core 300 can be created using a 3D printer from a soluble material. The soluble material may be sugar, starch, collagen, and/or a gel. The core may be solid, or porous. In an embodiment, the soluble material can be water soluble, such as sugar. An example, of a 3D printer that can print a core 300 from sugar is the ChefJet™ 3D printer made by 3D Systems. FIG. 3 illustrates an example of a core 300 made of a soluble material with a 3D printer using internal measurements from a patient's tracheal section. The tracheal section core 300 can contain all dimensions and all the individual unique contours 302, 304 of the patient. The core 300 can be fabricated with a lower density and a high level of porosity or hollow structure during the 3D printing process. The outer surfaces of the core 300 can be printed as a solid structure with a high level of anatomic detail. The sugar core 300 will be dissolved once the core 300 is no longer needed. A high porosity or hollow structure reduces the material needed to produce the core 300 and allows the solvent to penetrate the entire core 300 which will reduce the time needed to dissolve the core 300. Because the core 300 is a larger structure used to create an anatomically correct trachea for a patient, this construction is substantially different than other biological structures.

Once a core 300 is created, a covering that will become the insert can be placed on the surface of the core 300. In an embodiment, the covering can be a thin filament 400, a film, a plastic covering, or other thin sheet of material. The covering can have a uniform thickness and be sufficiently pliable to conform to the outer surface of the core 300, such that the topography of the inner surface of the covering becomes the topography of the outer surface of the covering. In different embodiments, different types of materials can be used for the covering. For example, in an embodiment, the covering is a thin filament 400. In another embodiment, the covering is a thin hot sheet of material.

Figure 4:
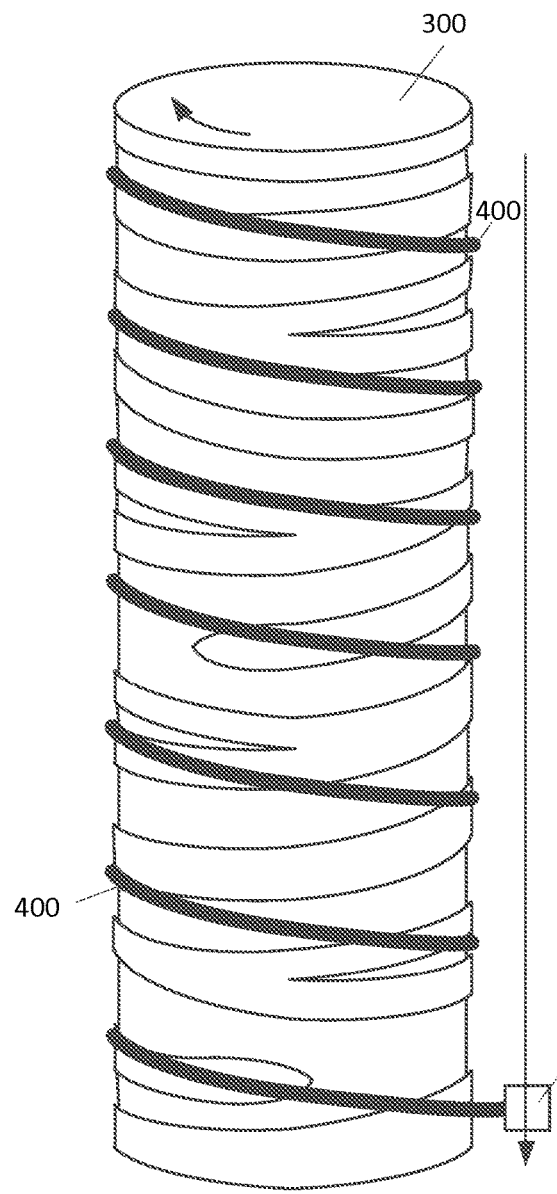
FIGS. 4-6 illustrate embodiments of a filament wrapped around the core.

The covering can be wrapped multiple times around the circumference of the core 300, as illustrated in FIG. 4. In an embodiment, the filament 400 may be a polylactic acid (PLA), or other bio-absorbable material. This filament 400 can be wrapped around the circumference of the core 300 in a helical fashion 404 along the length of the core 300. In an embodiment, the core 300 can be rotated while a filament 400 is extruded from a filament-dispensing nozzle 408. The outlet of the filament-dispensing nozzle 408 can be moved axially across the length of the rotating core 300 close to the surface of the core 300. In an embodiment, the filament-dispensing nozzle 408 can emit the hot and flexible filament 400 at a rate that matches the relative movement of the extruder outlet across the surface of the core 300.

Figure 5:
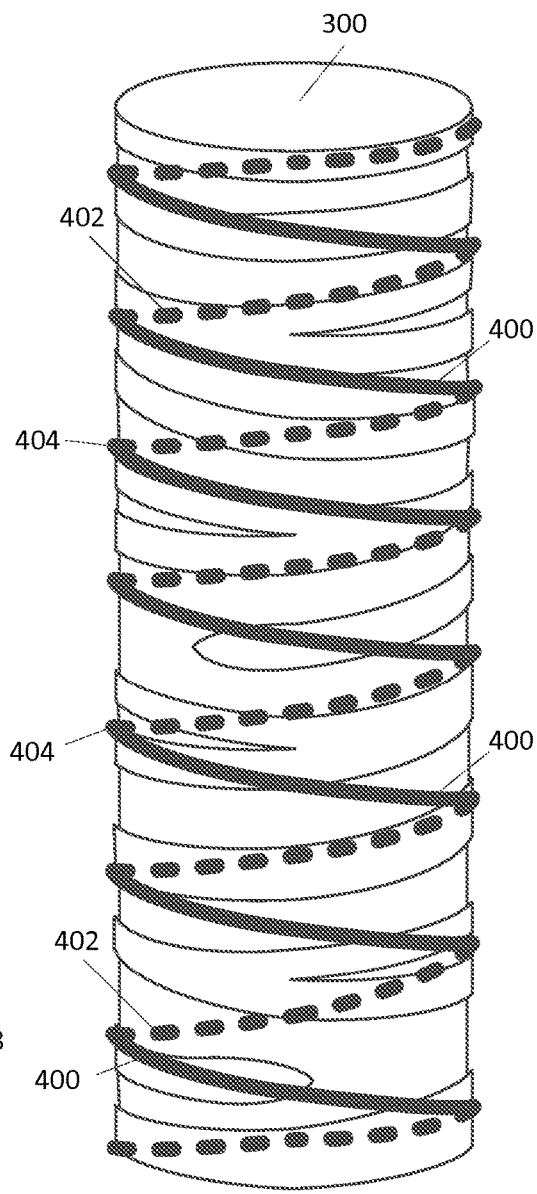
Figure 6:
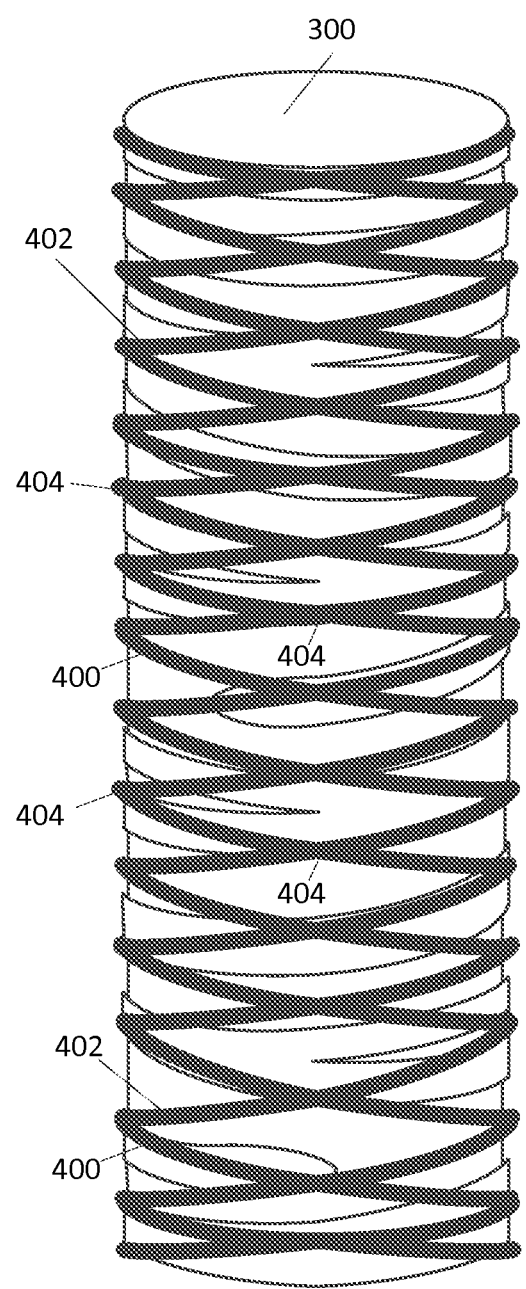

With reference to FIG. 5, a first portion of the filament 400 can be wrapped in a first helical direction around the core 300 and a second portion of the filament 402 (shown as a dashed line) can be wrapped around the core 300 in an opposite helical direction to form a crossed mesh filament pattern that is coupled at the overlapped points 404. As discussed, the filament 400 may be wrapped around the core 300 by rotating the core 300 in front of a filament-dispensing nozzle portion 408 of a material extruder to deposit a spiral of plastic strand 404 along the length of the core 300. Once the filament 400 reaches an end of the core 300, the core 300 can be rotated in another direction to continue depositing the filament 400 around the core 300 in order to generate a stint format 500. In an embodiment, additional filaments 400, 402 can be wrapped around the core 300 in an overlapped pattern with additional fused overlap points 404 to form a stronger custom medical implant as illustrated in FIG. 6.

In an embodiment, the filament 400, 402 can be a thermo plastic material. The filament 400, 402 can be wrapped on the core in a heated condition. When the filament 400, 402 cools it hardens around the core 300 in the shape of the outer surface of the core 300 to create a tubular insert 500. When the filament 400, 402 hardens, the filament strands that overlap each other can be securely fused together at these contact points 404 to each other. In an embodiment, the filament material 400, 402 is heated to a temperature between a glass transition temperature and a melting temperature for the filament. The over lapping filaments 400, 402 thermally bond portions of the filaments 400, 402 together. For example, if the filament 400, 402 is a polycarbonate, this filament material can soften by heating the filament to about 293 degrees Fahrenheit. Other filament materials will have different softening temperatures. The filaments 400, 402 can be heated above the softening temperature before being wrapped around the core 300 and then cooled to harden the filaments 400, 402 around the core 300.

In another embodiment, the covering can be created by dipping the core 300 into a liquid polymer which can then harden on the core 300. The liquid polymer can be a liquid thermoplastic which hardens when cooled. Alternatively, the liquid polymer can harden through a chemical reaction. Once the liquid polymer hardens, the core can be completely encapsulated by the hardened polymer. In order to expose the core 300 so that it can be dissolved, the hardened polymer could be cut at the ends to expose the ends of the soluble core 300 in order to dissolve it. In any embodiment, the outer surface of the covering will have features that closely match the inner surface of the covering, which matches the topography of the core 300 mold.

Figure 7:
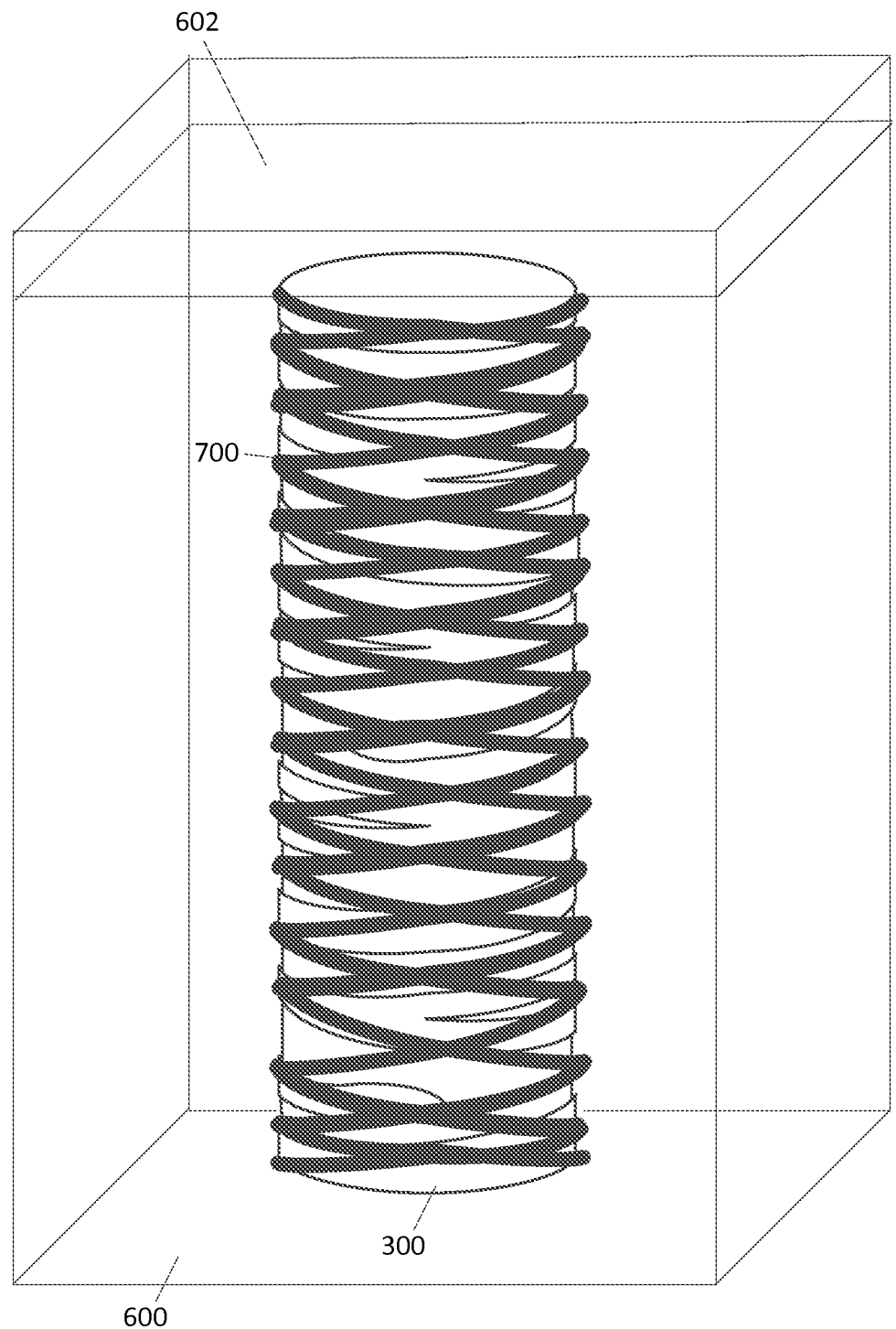
FIG. 7 illustrates an embodiment of an implant device formed on a core placed in a solvent filled container.
Figure 8:
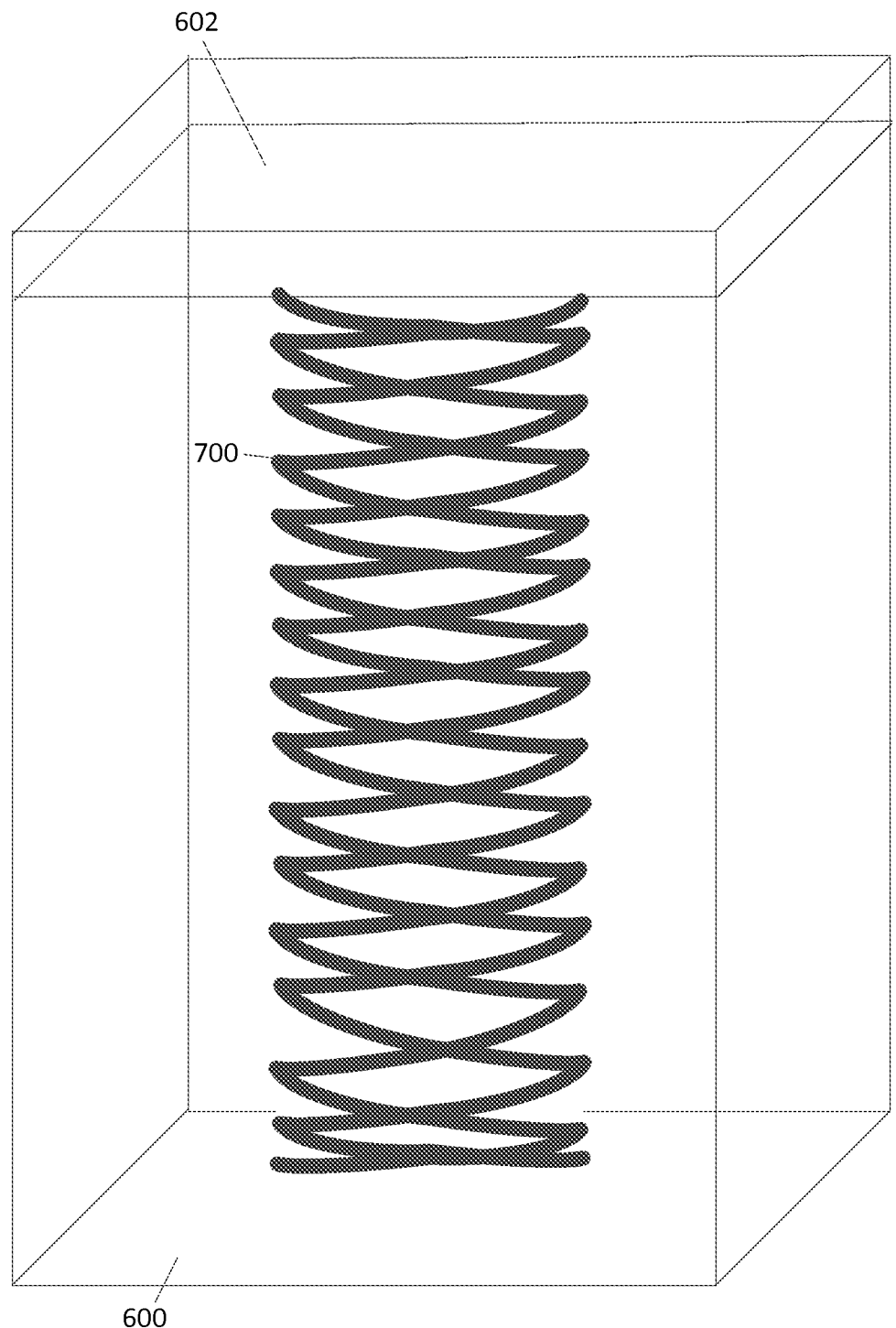
FIG. 8 illustrates an embodiment of the implant device that is left when the core has been dissolved by the solvent in the container.

Once the implant device 700 has been formed, the soluble material of the core 300 can be dissolved away to separate the implant device 700 from the core 300. In an embodiment, the core 300 material can be water soluble and the core 300 can be dissolved by submerging it in water, or otherwise exposing it to water. In some cases, the solubility can be related to water temperature and hot water can dissolve the core faster. In other embodiments, the core material can be soluble when exposed to other types of fluid solvents such as: tetrachloroethylene, toluene, turpentine, acetone, methyl acetate, ethyl acetate, hexane, petrol ether, citrus terpenes, etc. FIG. 7 illustrates a filament-wrapped core 300 in a container 600 holding a liquid solvent 602 such as water. The implant device 700 and core 300 can remain in the solvent filled container 600 until the core 300 dissolves away. Once dissolved, the core 300 can be removed from the implant device 700, as illustrated in FIG. 8.

The implant device 700 is removed from the core 300 and can be cleaned and modified in any manner before being inserted into the patient's inner cavity. Before insertion, the outer perimeter of the tubular implant 700 can be compressed in order to reduce the outer diameter of the implant 700 to facilitate insertion into the patient. The insert 702 can be compressed slightly, for example, a fraction of a centimeter, or several millimeters. The insert 702 can be compressed by the physician directly, or by inserting it into a tubular delivery device that will be used to deposit the implant 700 to the desired location in the patient. Once compressed, the implant 700 can be inserted into the inner cavity, and allowed to expand. In an embodiment, a properly sized implant 700 can be compressed against the inner surface of the cavity.

Figure 9:
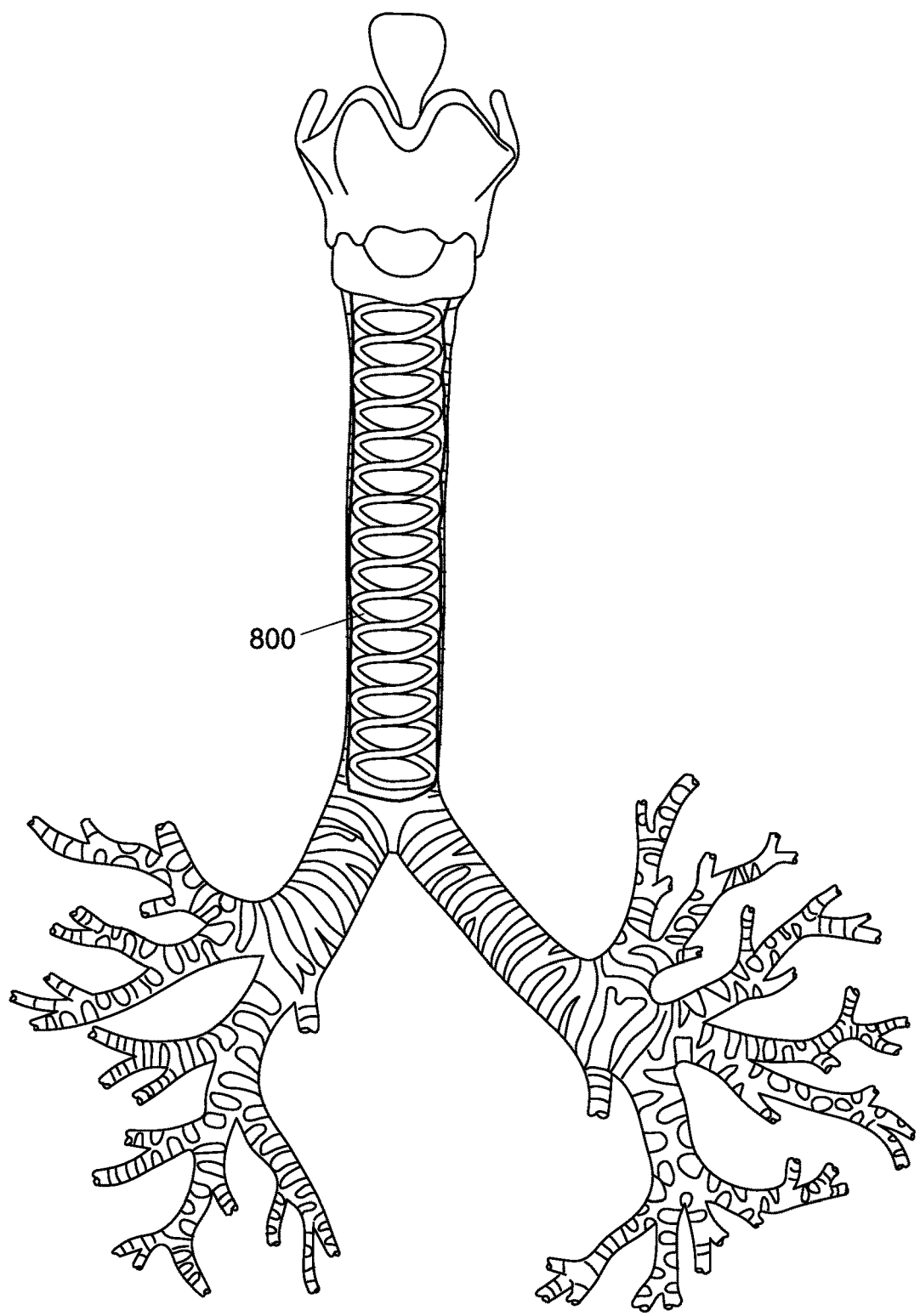
FIG. 9 illustrates the implant device placed in a human trachea.

In an embodiment, the tubular implant can be a tracheal stent 800, as illustrated in FIG. 9. The tracheal stent 800 can be compressed within a tubular delivery device. The delivery device can be inserted into the patient's trachea and positioned to deliver the tracheal stent 800 to the desired location with the contours of the tracheal stent 800 matching the internal anatomy of the corresponding internal surfaces of the patient's trachea. The delivery device can be extracted to precisely position the tracheal stent 800 within the trachea. Once inserted, the tracheal stent 800 will be allowed to expand and compress against the inner surface of the trachea 802.

In another embodiment, the filament 400 of the insert 700 can be absorbed by the trachea 200 and the strength of the trachea 200 can be improved. For example, a bioplastic filament material used to create the tracheal stent 800 can be a bioabsorbable material such as Polylactide (PLA) that can be absorbed by the patient and provide structural support to the trachea. In other embodiments, any other suitable filament material can be used to create bioabsorbable implant devices.

In other embodiments the implant device can be used for various other internal patient applications. For example, in an embodiment, the implant device may be custom designed and formed to fit within the inner body cavity that can be an artery. Again, the internal surface of the artery can be measured with an MRI or other machine. The MRI DICOM data can be converted to a 3D mesh and a 3D printer can be used to create a core made of a soluble material by sequentially depositing and fusing many parallel planar layers. The 3D printed core can have an outer surface that matches or closely corresponds to the inner surfaces of the artery. A filament(s) can be wrapped around the core to form the implant structure. The implant can be compressed and placed within a delivery device. The delivery device can be surgically inserted into the target location within the artery. The delivery device can then precisely release the implant so that the outer surface features of the implant are positioned adjacent to the corresponding anatomical features of the artery. Once in place, implant is allowed to expand and compress against the inner surface of the artery, keeping it open for blood flow.

It will be understood that the inventive system has been described with reference to particular embodiments, however additions, deletions and changes could be made to these embodiments without departing from the scope of the inventive system. Although the systems that have been described include various components, it is well understood that these components and the described configuration can be modified and rearranged in various other configurations.

What is claimed is:

1. A method for creating a tubular insert comprising:
    obtaining surface measurements for an internal surface of a portion of a patient;
    using the surface measurements to create a core design having non-uniform surfaces;
    3D printing a porous core with a water soluble sugar from the core design;
    wrapping a thermoplastic filament multiple times around a circumference of the porous core in a first helical direction and a second helical direction that is opposite the first helical direction wherein the second helical direction forms an overlapped pattern with the first helical direction and a plurality of fused overlap points are formed where the second helical direction crosses over the first helical direction;

hardening the filament to create a tubular insert;

placing the porous core in water to dissolve at least a portion of the porous core; and separating the tubular insert from the porous core.

2. The method of claim 1 wherein the internal surface is within a trachea of the patient, further comprising:

compressing the tubular insert to reduce an outer diameter of the tubular insert;

inserting the tubular insert into the trachea; and allowing the tubular insert to expand and compress against the inner surface of the trachea.

3. The method of claim 1 wherein the internal surface is within an artery of the patient, further comprising:

compressing the tubular insert to reduce an outer diameter of the tubular insert;

inserting the tubular insert into the artery; and allowing the tubular insert to expand and compress against the inner surface of the artery.

4. The method of claim 1 further comprising:

heating the filament to a temperature between a glass transition temperature and a melting temperature for the filament; and thermally bonding a first portion of the filament to a second portion of the filament.

5. The method of claim 1 further comprising: absorbing the filaments by the trachea, wherein the filament material is a bioplastic material.

6. A method for creating a tubular insert comprising:

obtaining magnetic resonance imaging (Mill) data for a portion of a patient;

converting the MRI data into 3D mesh data for an internal surface of the portion of the patient;

using surface measurements of the internal surface to create a core design having non-uniform surfaces;

3D printing a porous core with a water soluble sugar from the core design;

wrapping a thermoplastic filament multiple times around a circumference of the porous core in a first helical direction and a second helical direction that is opposite the first helical direction wherein the second helical direction forms an overlapped pattern with the first helical direction and a plurality of fused overlap points are formed where the second helical direction crosses over the first helical direction;

hardening the filament to create a tubular insert;

placing the porous core in water to dissolve at least a portion of the porous core; and separating the tubular insert from the porous core.

7. The method of claim 6 wherein the internal surface is within a trachea of the patient, further comprising:

compressing the tubular insert to reduce an outer diameter of the tubular insert;

inserting the tubular insert into the trachea; and allowing the tubular insert to expand and compress against the inner surface of the trachea.

8. The method of claim 6 wherein the internal surface is within an artery of the patient, further comprising:

compressing the tubular insert to reduce an outer diameter of the tubular insert;

inserting the tubular insert into the artery; and allowing the tubular insert to expand and compress against the inner surface of the artery.

9. The method of claim 6 further comprising:

heating the filament to a temperature between a glass transition temperature and a melting temperature for the filament; and thermally bonding a first portion of the filament to a second portion of the filament.

10. The method of claim 6 further comprising:

absorbing the filament by the trachea, wherein the filament material is a bioplastic material.

11. A method for creating a tubular insert comprising:

obtaining surface measurements for an internal surface of a patient having a branch configuration;

using the surface measurements to create a core design having the branch configuration;

3D printing a porous core with a soluble material from the core design;

wrapping a thermoplastic filament multiple times around a circumference of the porous core in a first helical direction and a second helical direction that is opposite the first helical direction wherein the second helical direction forms an overlapped pattern with the first helical direction and a plurality of fused overlap points are formed where the second helical direction crosses over the first helical direction;

hardening the filament to create a tubular insert;

placing the porous core in water to dissolve at least a portion of the porous core; and separating the tubular insert from the porous core.

12. The method of claim 11 wherein the internal surface is within a trachea and bronchial tubes of the patient, further comprising:

compressing the tubular insert to reduce an outer diameter of the tubular insert;

inserting the tubular insert into the trachea and the bronchial tubes; and allowing the outer diameter of the tubular to compress the outer diameter of the tubular insert against the inner surface of the trachea and the bronchial tubes.

13. The method of claim 11 wherein the internal surface is within an artery of the patient, further comprising:

compressing the tubular insert to reduce an outer diameter of the tubular insert;

inserting the tubular insert into the artery; and allowing the tubular insert to expand and compress against the inner surface of the artery.

14. The method of claim 11 further comprising:

heating the filament to a temperature between a glass transition temperature and a melting temperature for the filament; and thermally bonding a first portion of the filament to a second portion of the filament.

15. The method of claim 11 further comprising:

absorbing the filament by the trachea, wherein the filament material is a bioplastic material.

* * * * *